(12) United States Patent
Furman et al.

(10) Patent No.: US 7,714,998 B2
(45) Date of Patent: *May 11, 2010

(54) IMAGE SPLITTING IN OPTICAL INSPECTION SYSTEMS

(75) Inventors: Dov Furman, Rehovot (IL); Roy Kaner, Tel-Aviv (IL); Ori Gonen, Tel-Aviv (IL); Daniel Mandelik, Rehovot (IL); Eran Tal, Petah-tikva (IL); Shai Silberstein, Rishon-Le-Zion (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 11/944,684

(22) Filed: Nov. 26, 2007

(65) Prior Publication Data

US 2008/0137074 A1 Jun. 12, 2008

Related U.S. Application Data

(60) Provisional application No. 60/861,303, filed on Nov. 28, 2006.

(51) Int. Cl.
*G01N 21/00* (2006.01)
(52) U.S. Cl. .................. 356/237.2; 356/237.5
(58) Field of Classification Search .... 356/237.1–241.6
See application file for complete search history.

(56) References Cited

U.S. PATENT DOCUMENTS 2,045,093 A 6/1936 Newcomer
2,559,698 A 7/1951 Bahre
2,736,250 A 2/1956 Papritz (Continued)

FOREIGN PATENT DOCUMENTS

JP 61262607 11/1986

(Continued)

OTHER PUBLICATIONS

Office Action dated Mar. 5, 2009, from U.S. Appl. No. 11/944,677 (filed Nov. 26, 2007), 16 pages.

(Continued)

*Primary Examiner*—Gregory J Toatley, Jr.
*Assistant Examiner*—Jarreas C Underwood
(74) *Attorney, Agent, or Firm*—Sonnenschein Nath & Rosenthal LLP

(57) ABSTRACT

In an optical inspection tool, an image of an object under inspection, such as a semiconductor wafer, may be obtained using imaging optics defining a focal plane. Light comprising the image can be split into portions that are detected using multiple detectors which each register a portion of the image. The image of the object at the focal plane can be split into two, three, or more parts by polarization-based beam splitters and/or lenses positioned tangent to the focal plane. The splitting apparatus may comprise a pair of arrays of half-cylinder lenses comprising a convex side and a flat side. The arrays can be positioned with the cylinder axes perpendicular to one another and the flat sides facing each other. Thus, the pair of arrays can divide incoming light into a plurality of rectangular portions without introducing non-uniformities which would occur if several spherical lenses are configured for use in a rectangular array.

22 Claims, 12 Drawing Sheets

U.S. PATENT DOCUMENTS

| | | | |
|---|---|---|---|
| 3,211,046 A * | 10/1965 | Kennedy | 359/219 |
| 3,598,457 A | 8/1971 | Pearson | |
| 3,652,167 A * | 3/1972 | Smith | 356/636 |
| 3,668,406 A | 6/1972 | Reid et al. | |
| 3,768,910 A * | 10/1973 | Zanoni | 356/624 |
| 4,011,403 A | 3/1977 | Epstein et al. | |
| 4,078,860 A | 3/1978 | Globus et al. | |
| 4,247,203 A | 1/1981 | Levy et al. | |
| 4,323,925 A * | 4/1982 | Abell et al. | 348/340 |
| 4,347,001 A | 8/1982 | Levy et al. | |
| 4,360,372 A | 11/1982 | Maciejko | |
| 4,378,159 A | 3/1983 | Galbraith | |
| 4,383,170 A | 5/1983 | Takagi et al. | |
| 4,456,339 A * | 6/1984 | Sommargren | 359/497 |
| 4,462,662 A | 7/1984 | Lama | |
| 4,486,776 A | 12/1984 | Yoshida | |
| 4,556,317 A | 12/1985 | Sandland et al. | |
| 4,556,791 A * | 12/1985 | Spillman, Jr. | 250/225 |
| 4,579,455 A | 4/1986 | Levy et al. | |
| 4,589,030 A * | 5/1986 | Kley | 348/367 |
| 4,589,736 A | 5/1986 | Harrigan et al. | |
| 4,597,665 A | 7/1986 | Galbraith et al. | |
| 4,601,576 A | 7/1986 | Galbraith | |
| 4,618,938 A | 10/1986 | Sandland et al. | |
| 4,639,587 A | 1/1987 | Chadwick et al. | |
| 4,644,172 A | 2/1987 | Sandland et al. | |
| 4,734,923 A | 3/1988 | Frankel et al. | |
| 4,760,265 A | 7/1988 | Yoshida et al. | |
| 4,766,324 A | 8/1988 | Saadat et al. | |
| 4,806,774 A | 2/1989 | Lin et al. | |
| 4,845,558 A | 7/1989 | Tsai et al. | |
| 4,877,326 A | 10/1989 | Chadwick et al. | |
| 4,898,471 A | 2/1990 | Stonestrom et al. | |
| 4,967,095 A | 10/1990 | Berger et al. | |
| 4,969,198 A | 11/1990 | Batchelder et al. | |
| 5,008,743 A | 4/1991 | Katzir et al. | |
| 5,016,109 A * | 5/1991 | Gaylord | 348/218.1 |
| 5,029,975 A | 7/1991 | Pease | |
| 5,056,765 A | 10/1991 | Brandstater | |
| 5,058,982 A | 10/1991 | Katzir | |
| 5,076,692 A | 12/1991 | Neukermans et al. | |
| 5,112,129 A | 5/1992 | Davidson et al. | |
| 5,153,668 A | 10/1992 | Katzir et al. | |
| 5,161,238 A | 11/1992 | Mehmke | |
| 5,194,959 A * | 3/1993 | Kaneko et al. | 348/335 |
| 5,264,912 A | 11/1993 | Vaught et al. | |
| 5,267,017 A | 11/1993 | Uritsky et al. | |
| 5,352,886 A * | 10/1994 | Kane | 250/216 |
| 5,381,004 A | 1/1995 | Uritsky et al. | |
| 5,381,439 A | 1/1995 | English, Jr. et al. | |
| 5,386,228 A | 1/1995 | Okino | |
| 5,422,724 A | 6/1995 | Kinney et al. | |
| 5,519,675 A | 5/1996 | Toofan | |
| 5,537,168 A | 7/1996 | Kitagishi et al. | |
| 5,537,669 A | 7/1996 | Evans et al. | |
| 5,586,058 A | 12/1996 | Aloni et al. | |
| 5,604,585 A | 2/1997 | Johnson et al. | |
| 5,608,155 A | 3/1997 | Ye et al. | |
| 5,617,203 A | 4/1997 | Kobayashi et al. | |
| 5,619,429 A | 4/1997 | Aloni et al. | |
| 5,619,588 A | 4/1997 | Yolles et al. | |
| 5,659,172 A | 8/1997 | Wagner et al. | |
| 5,687,152 A * | 11/1997 | Takeda et al. | 369/112.07 |
| 5,699,447 A | 12/1997 | Alumot et al. | |
| 5,774,444 A | 6/1998 | Shimano et al. | |
| 5,797,317 A | 8/1998 | Lahat et al. | |
| 5,798,829 A | 8/1998 | Vaez-Iravani | |
| 5,822,055 A | 10/1998 | Tsai et al. | |
| 5,825,482 A | 10/1998 | Nikoonahad et al. | |
| 5,835,278 A * | 11/1998 | Rubin et al. | 359/636 |
| 5,864,394 A | 1/1999 | Jordan, III et al. | |
| 5,883,710 A | 3/1999 | Nikoonahad et al. | |
| 5,892,579 A | 4/1999 | Elyasaf et al. | |
| 5,907,628 A | 5/1999 | Yolles et al. | |
| 5,912,735 A | 6/1999 | Xu | |
| 5,917,588 A | 6/1999 | Addiego et al. | |
| 5,939,647 A | 8/1999 | Chinn et al. | |
| 5,970,168 A | 10/1999 | Montesanto et al. | |
| 5,982,921 A | 11/1999 | Alumot et al. | |
| 5,991,699 A | 11/1999 | Kulkarnu et al. | |
| 6,020,957 A | 2/2000 | Rosengaus et al. | |
| 6,021,214 A | 2/2000 | Evans et al. | |
| 6,064,517 A | 5/2000 | Chuang et al. | |
| 6,075,375 A | 6/2000 | Burkhart et al. | |
| 6,078,386 A | 6/2000 | Tsai et al. | |
| 6,099,596 A | 8/2000 | Li et al. | |
| 6,100,976 A * | 8/2000 | Ackerson | 356/336 |
| 6,122,046 A | 9/2000 | Almogy | |
| 6,124,924 A | 9/2000 | Feldman et al. | |
| 6,137,535 A * | 10/2000 | Meyers | 348/340 |
| 6,169,282 B1 | 1/2001 | Maeda et al. | |
| 6,172,349 B1 | 1/2001 | Katz et al. | |
| 6,175,645 B1 | 1/2001 | Elyasaf et al. | |
| 6,175,646 B1 | 1/2001 | Schemmel et al. | |
| 6,178,257 B1 | 1/2001 | Alumot et al. | |
| 6,208,411 B1 | 3/2001 | Vaez-Iravani | |
| 6,208,750 B1 | 3/2001 | Tsada | |
| 6,215,551 B1 | 4/2001 | Nikoonahad et al. | |
| 6,236,454 B1 | 5/2001 | Almogy | |
| 6,246,822 B1 | 6/2001 | Kim et al. | |
| 6,256,093 B1 | 7/2001 | Ravid et al. | |
| 6,267,005 B1 | 7/2001 | Samsavar et al. | |
| 6,268,093 B1 | 7/2001 | Kenan et al. | |
| 6,268,916 B1 | 7/2001 | Lee et al. | |
| 6,271,916 B1 | 8/2001 | Marxer et al. | |
| 6,274,878 B1 | 8/2001 | Li et al. | |
| 6,288,780 B1 | 9/2001 | Fairley et al. | |
| 6,317,514 B1 | 11/2001 | Reinhorn et al. | |
| 6,324,298 B1 | 11/2001 | O'Dell et al. | |
| 6,347,173 B1 | 2/2002 | Suganuma et al. | |
| 6,360,005 B1 | 3/2002 | Aloni et al. | |
| 6,361,910 B1 | 3/2002 | Sarig et al. | |
| 6,366,315 B1 | 4/2002 | Drescher | |
| 6,369,888 B1 | 4/2002 | Karpol et al. | |
| 6,456,769 B1 | 9/2002 | Furusawa et al. | |
| 6,542,304 B2 | 4/2003 | Tacklind et al. | |
| 6,628,681 B2 | 9/2003 | Kubota et al. | |
| 6,633,375 B1 | 10/2003 | Veith et al. | |
| 6,819,490 B2 * | 11/2004 | Sandstrom et al. | 359/566 |
| 6,892,013 B2 | 5/2005 | Furman et al. | |
| 6,895,149 B1 | 5/2005 | Jacob et al. | |
| 7,190,519 B1 * | 3/2007 | Kitagishi | 359/485 |
| 7,218,389 B2 | 5/2007 | Uto et al. | |
| 2001/0033386 A1 | 10/2001 | Kranz et al. | |
| 2002/0037099 A1 | 3/2002 | Ogawa et al. | |
| 2002/0067478 A1 | 6/2002 | Karpol et al. | |
| 2003/0227618 A1 | 12/2003 | Some | |
| 2004/0032581 A1* | 2/2004 | Nikoonahad et al. | 356/237.2 |
| 2004/0146295 A1* | 7/2004 | Furman et al. | 398/9 |
| 2005/0084766 A1 | 4/2005 | Sandstrom | |
| 2008/0037933 A1 | 2/2008 | Furman et al. | |

FOREIGN PATENT DOCUMENTS

| | | |
|---|---|---|
| WO | WO 00/70332 | 11/2000 |

OTHER PUBLICATIONS

Response from Office Action filed Aug. 5, 2009, from U.S. Appl. No. 11/944,677 (filed Nov. 26, 2007), 7 pages.

Office Action dated Apr. 6, 2006, from EP Patent Application No. EP 03 250 255.1, 8 pages.

Patent Abstracts of Japan, vol. 17, No. 613, Jul. 1993 & JP 05 190421.

Patent Abstracts of Japan. vol. 1996, No. 10, Jun. 1996 & JP 08 154210.

Patent Abstracts of Japan. vol, 1999, No. 4, Jan. 1999 & JP 11 014357.

Patent Abstracts of Japan, vol. 1997, No. 3, Nov. 1996 & JP 08 292361.

T.S. McKecknie, Speckle Reduction, pp, 123-170 in Topics in Applied Physics, vol. 9, Laser Speckle and Related Phenomena, edited by J.C. Dainty, Springer Verlag.

D. Kohler et al, Speckle Reduction in Pulsed-Laser Photography, published in Optics Communications, vol. 12, No. 1, pp. 24-28, Sep. 1974.

Dingel et al., Speckle Reduction with Virtual Incoherent Laser illumination Using Modified Fiber Array, published in Optik, vol. 94, No. 3, pp. 132-136, 1993,.

Dom, Byron et al., Machine Vision and Applications, 1998, 1:205-221.

NEGETECH, EP 03250255, EP Search Report, Apr. 22, 2003, 5 pp.

U.S. Provisional Patent Application No. 60/415,082 filed Sep. 30, 2002.

* cited by examiner

IMAGE SPLITTING IN OPTICAL INSPECTION SYSTEMS

PRIORITY CLAIM

This application claims priority to U.S. Provisional Patent Application No. 60/861,303, filed Nov. 28, 2006 and entitled IMAGE SPLITTING IN OPTICAL INSPECTION SYSTEMS, which is hereby incorporated by reference herein in its entirety.

BACKGROUND

In wafer inspection systems which utilize two dimensional imaging, the inspection speed is determined, among other things, from parameters including field of view size, and time between imaging sequential images. Generally speaking, a larger field of view, or a shorter time between sequential images will increase the inspection speed.

Decreasing the time between imaging may be complicated and expensive. For instance, decreasing the time between images can require very fast detectors (much faster above normal 30 Hz detectors), fast illumination (for example, repetitive laser with hundreds of pulses per second), and a fast stage or other suitable components for generating relative motion between the wafer and imaging components to change which portion(s) of the wafer are in view for imaging.

A more preferable approach in some circumstances is to enlarge the field of view. However, when fine resolution is required (pixel size in the wafer plane is below 0.5 microns), the detector must contain a numerous pixels. For example, using 0.2 micron pixel, and a conventional commercial detector with 2K×2K pixels, the field of view is only 0.4 mm×0.4 mm. An enlarged field of view may also require a faster stage or other suitable components for providing relative motion between the imaging components and the wafer.

The image view can be increased by using multiple two dimensional detectors to obtain an image, with the image divided amongst the detectors. Some currently-existing systems split an image before the focal plane of the other optics used to obtain the image using, for instance, beam splitters and/or mirrors. See, for instance, U.S. patent application Ser. No. 10/345,097, filed Jan. 15, 2003, and published as U.S. Patent Application Publication No., 20040146295 which are each incorporated by reference in their entireties herein. However, splitting an image by a mirror or other element(s) before the focal plane may be problematic in some instances. The problems may include, for example, reductions in intensity and/or non-uniform intensity.

FIG. 9 illustrates an example wherein the intensity in some parts of a split image is reduced when some rays are reflected back from the mirror and do not actually reach the focal plane, since the actual splitting of the image occurs prior to the focal plane. As shown in FIG. 9, three rays (R1, R2 and R3) from the imaging optics 18 of an inspection system reach point A in the focal plane $FP_{18}$ of the imaging optics if no splitting mirror is used (i.e., if the mirror shown in FIG. 9 is disregarded, all three rays reach point A). However, when the splitting mirror comprising reflective planes 902 and 904 is used, only two rays (R2 and R3) reach the detectors 908-1 and 908-2 in the split focal plane. The top ray (R1) is reflected back from the mirror.

FIG. 9 also illustrates an example of non uniform intensity that may result from splitting. The intensity reduction is position dependent—a given portion of the image that is closer to the splitting point will have a reduced intensity relative to a portion of the image far from the splitting point. In FIG. 9, point B' gets only about half of the rays (i.e. rays generally emanating from the bottom half part of the imaging optics), while point A', for example, gets more (about two thirds: from ray R2 to R3).

An example hypothetical intensity distribution in detector 908-1 and 908-2 imaging a uniform input image (I and II) is shown in FIG. 10. The image is darker at points closer to the splitting point, with denser cross-hatching representing progressively darker portions of the image (becoming darker from left to right in 908-2 and right to left in 908-1).

The angular distribution of the image is not preserved when an image is split in this manner. For a wafer inspection system, the angular distribution of the scattered or reflected light from the wafer contains information regarding the wafer characteristics. Using splitting mirrors before the focal plane changes the angular distribution since it blocks a range of ray angles and thus may result in reduced inspection accuracy.

When splitting by beam splitters, some of the rays (usually 50%) are reflected from the beam splitter while the rest of the rays are transmitted. This way does not break the uniformity or the angular distribution, but the intensity is reduced by 50%. When using more than one splitter to split an image into more than two portions, the intensity can be reduced even more.

SUMMARY

In embodiments of the present subject matter, an image can be split into two, three, or more parts by suitable elements such as beam splitters and/or lenses. The elements may be positioned tangent to the focal plane of an inspection tool's imaging apparatus, may intersect with the focal plane, or may be positioned past the focal plane. By splitting in this manner, non-uniformities, such as those that occur at the edges of detectors when images are split using mirrors, can be reduced or avoided. Furthermore, as set forth in more detail below, light loss can also be reduced through the use of appropriately-configured beam splitters and/or lenses.

The image splitting components are placed within a wafer or other inspection tool comprising one or more imaging components that obtain an image of an object at a focal plane. Although several examples herein discuss wafer inspection, the presently-disclosed technology may be used for inspection of any kind of object(s) including, but not limited to, reticles, photomasks, flat panel displays, printed circuit boards, etc. Furthermore, the image splitting components and other presently-disclosed teachings may be used in conjunction with inspection tools other than the tool described in the above-mentioned U.S. patent application Ser. No. 10/345,097.

An inspection system can include at least two two-dimensional detectors, where the image at the focal plane is split between at least some of the detectors using at least one splitting apparatus and at least one point of the at least one splitting apparatus is placed within the focal plane.

An optical inspection system configured to create an image of an object at a focal plane can comprise a set of imaging optics which create the image of the object at the focal plane. For instance, the imaging optics can collect light scattered, deflected, and/or diffracted by the object and focus the light. The optical inspection system can further comprise at least two two-dimensional detectors. The inspection system can comprise at least one splitting apparatus positioned at the focal plane, the splitting apparatus configured to split the image of the object at the focal plane into a plurality of portions and to direct at least one portion to a two-dimensional detector. Thus, the two-dimensional detectors can act as an optically continuous surface, with each detector used to register light comprising different parts of the image.

In some embodiments, the splitting apparatus can comprise components that change the polarization state of light comprising the image. For instance, an array of components can be used to change the polarization of different portions of the light corresponding to different parts of the image polarization so that at least one portion has a different polarization from another portion. In some embodiments, the splitting apparatus can comprise a beam splitter, with the beam splitter configured to direct at least one portion of light to a detector based on the polarization state of the light. For example, light of one polarization may be directed towards one or more detectors, while light of another polarization may be directed towards one or more different detectors. In some embodiments, the array of components may be configured to rotate the polarization of light entering the components. The components may be positioned so that the difference between rotation angles imparted by a pair of adjacent components in the array is ninety degrees. In some embodiments, the array is two-dimensional and may be arranged in a checkered pattern.

In some embodiments, one or more filter(s) or other suitable polarizing element(s) can be positioned to polarize light comprising the image of the object before the light reaches the array of components.

In some embodiments, a splitting apparatus comprises an array of lenses. The lenses may, for instance, be arranged in a two-dimensional lens array. Any suitable type or types of lenses can be used. For instance, graded index lenses may be used in some embodiments. In other embodiments, the lenses may comprise diffractive lenses, either in a two-dimensional array or in another arrangement. Regardless of the type of lenses, in some embodiments, the splitting apparatus can comprise at least two arrays, with the arrays arranged sequentially.

In some embodiments, the splitting apparatus can comprise an array of at least partially cylindrical lenses positioned alongside one another. For example, the splitting apparatus may comprise two arrays of at least partially cylindrical lenses, with the arrays positioned sequentially. The cylindrical lenses can comprise diffractive lenses and/or graded index lenses in some embodiments.

In some embodiments, when cylindrical lens arrays are used, each cylinder in the array can comprise at least one convex side comprising a surface which curves outward about an axis. In some embodiments, each cylinder can comprise a flat side opposite the convex side. The cylinders of the array can positioned so that the respective axes are parallel to one another. When multiple arrays are used, a first and second array can be positioned so that the flat sides of the cylinders in the first array face the flat sides of the cylinders of the second array. In some embodiments, the first and second arrays may be configured so that the axes of the cylinders of the first array are at an angle relative to the axes of the cylinders of the second array. For instance, the angle may be at or near ninety degrees such that the axes of the cylinders of the first array are positioned substantially perpendicular to the axes of the cylinders of the second array.

Splitting apparatus of the present subject matter can be used in any inspection tool. For instance, the tool can comprise at last one illumination source and a transporter configured to impart relative motion between the object and the focal plane so that the portion of the object that is in view of the focal plane can be varied. For instance, the transporter can comprise a stage that moves the object. In other embodiments, the transporter can comprise rotating mirrors or other components that vary the field of view without relying on motion of the object. In some embodiments, the illumination source can comprise a laser configured to illuminate the object with polarized light. The polarization may be a feature of the laser (or other) illumination used. However, polarized illumination may be additionally or alternatively achieved in other ways, such as via one or more polarization filters or elements. The polarization filters or elements can be placed at any suitable location(s), including, but not limited to, between the illumination source and the object.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended figures, in which:

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the instant disclosure includes modifications and variations as come within the scope of the appended claims and their equivalents.

Figure 7:
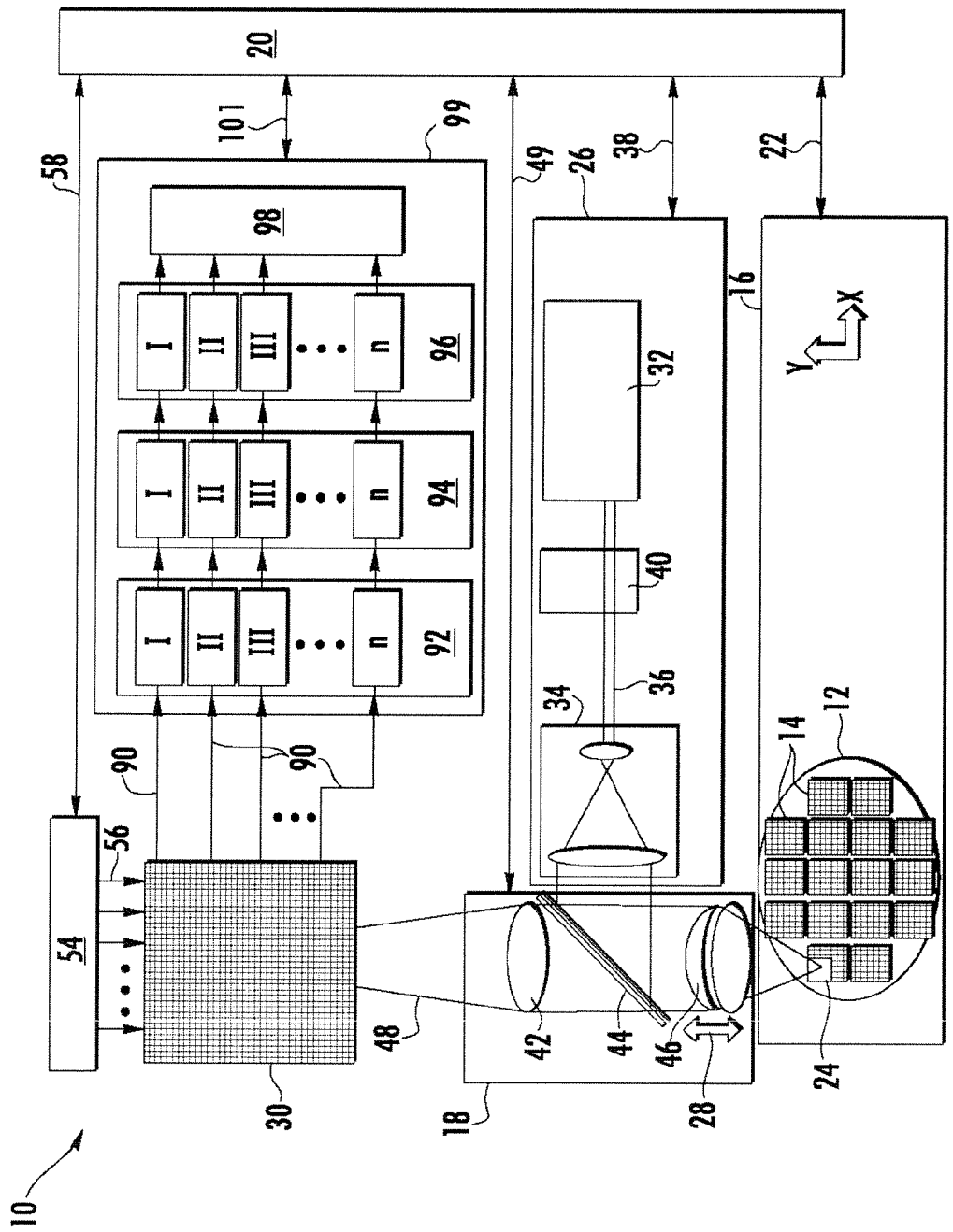
FIG. 7 is a block diagram showing illumination, imaging, and control components in an exemplary optical inspection tool.
Figure 8:
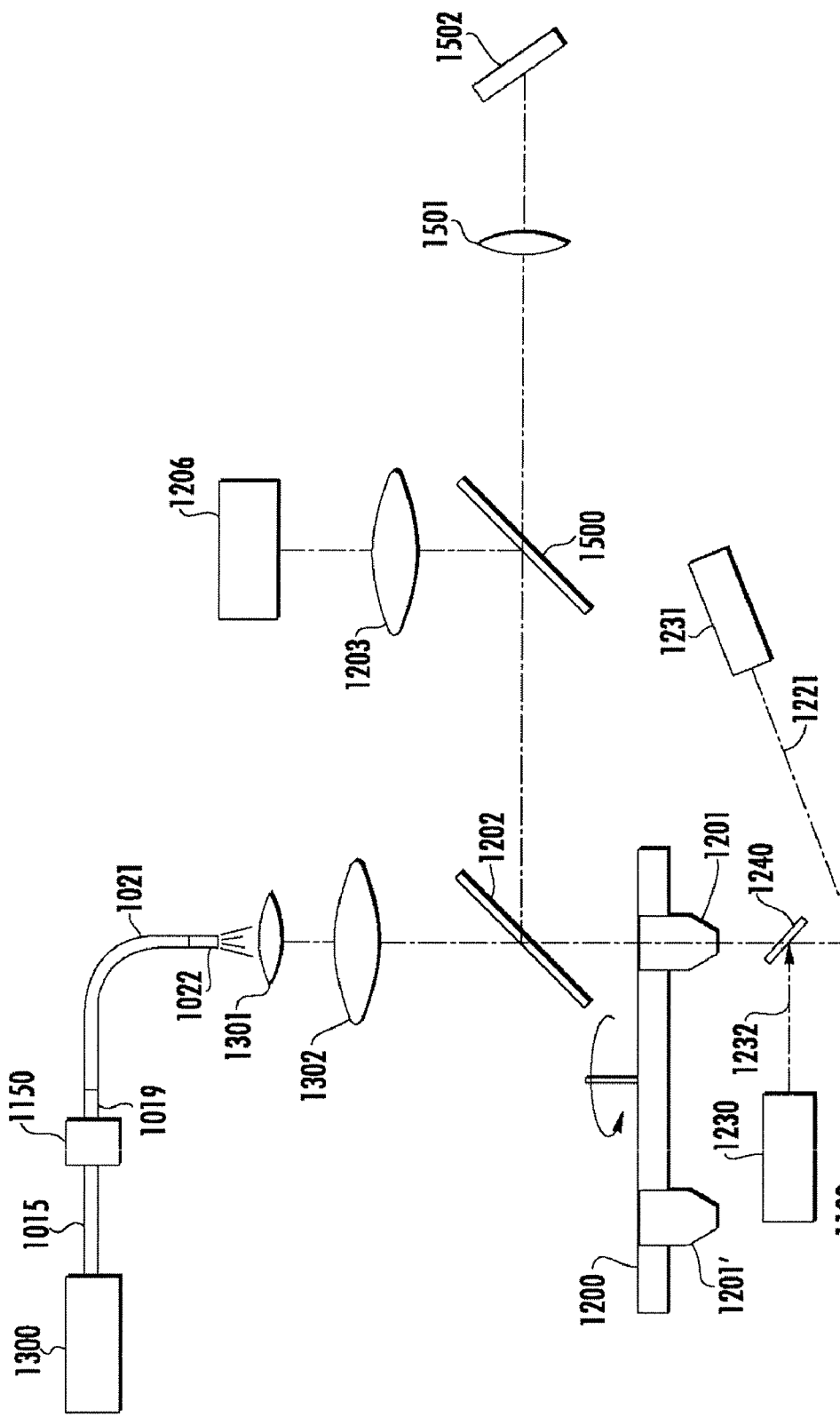
FIG. 8 is a block diagram showing additional aspects of imaging and illumination in an exemplary optical inspection tool.
Figure 9:
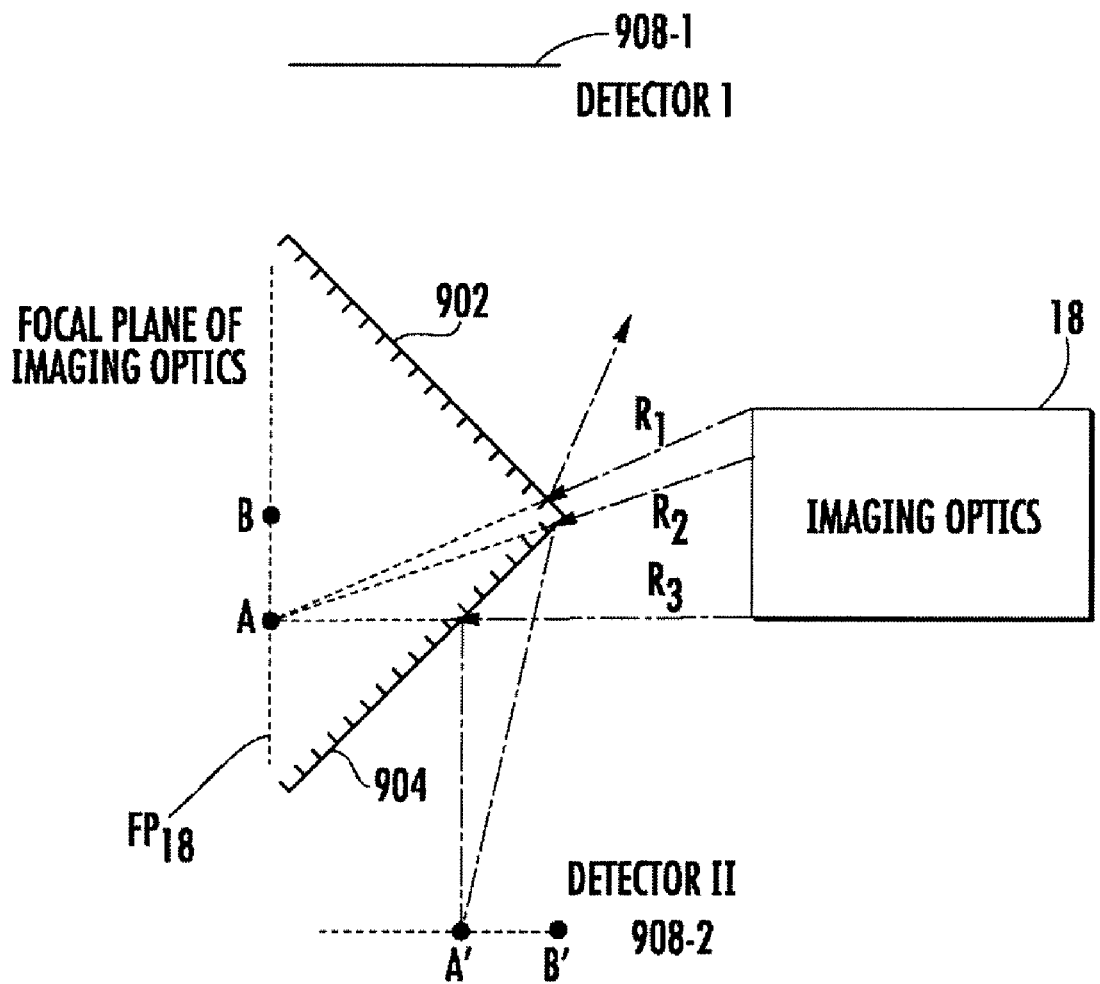
FIG. 9 is an illustration depicting an example where all splitting occurs before the focal plane of a set of imaging optics.
Figure 10:
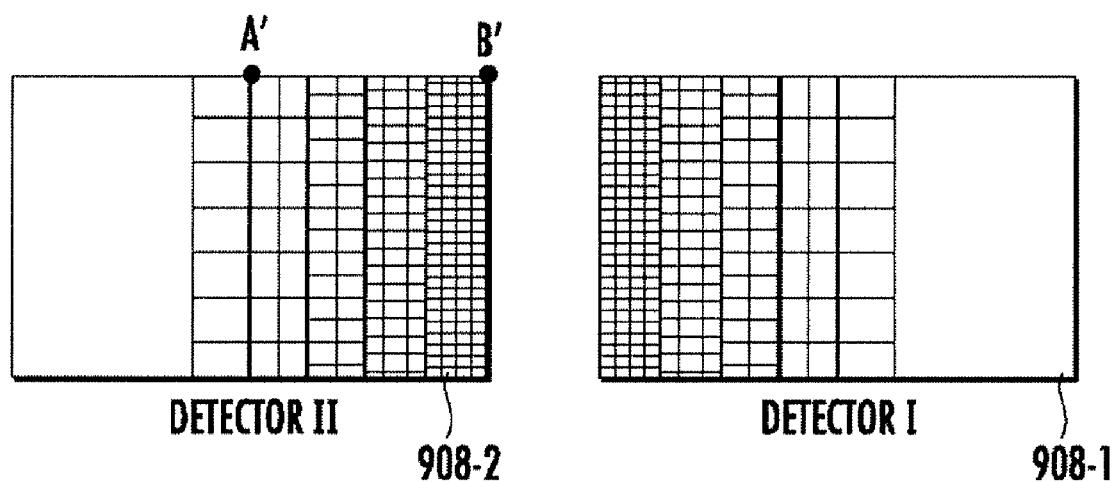
FIG. 10 is an illustration of exemplary hypothetical detector non-uniformities which may be introduced when all splitting occurs before the focal plane Use of like reference numerals in different features is intended to illustrate like or analogous components.

Before discussing exemplary embodiments of splitting apparatuses, FIGS. 7 and 8 will be discussed to place the splitting apparatus in context. In this example, FIG. 7 is a schematic diagram illustrating an exemplary embodiment of a system for fast on-line electro-optical detection of wafer defects, while FIG. 8 shows a schematic illustration of an object inspection system utilizing a laser source and a fiber optical delivery bundle in an exemplary inspection tool. For instance, the tool may comprise a Negevtech 3200 optical inspection tool (available from Negevtech, Ltd. of Rehovot, Israel), modified to use one or more embodiments of the presently disclosed splitting apparatus and methodologies. Additional details regarding exemplary aspects of an optical inspection system can be found in U.S. patent application Ser. No. 10/345,097. However, it is to be noted that the image splitting principles discussed below can be used in any suitable inspection system that creates an image of an object at a focal plane.

As shown in FIG. 7, an inspection tool can include a focal plane assembly 30 comprising pixels from multiple two-dimensional detectors. Focal plane assembly 30 is configured so that a continuous surface of photodetectors is optically formed at the focal plane of imaging optics 18. The actual photodetectors can be located at different geometric locations. In embodiments of the present subject matter, the inspection image obtained at the focal plane of imaging optics 18 can be split using one or more embodiments of a splitting apparatus as discussed in the examples below.

In operation, the dies 14 of wafer 12 can be illuminated in any suitable manner, such as by laser light from pulsed illumination system 26. Light 48 represents rays of light scattered, reflected, and diffracted by the wafer. This light can be collected using imaging optics 18. In this example, imaging optics 18 comprise a beam splitter 44 (used in illuminating wafer 12 with light from laser system 26), focusing lens 42, and an objective lens 46 which may be adjusted using an auto-focus system 28 (not shown in detail). In this example, focusing lens 42 focuses light 48 onto focal plane assembly 30 and defines the focal plane of imaging optics 18, referred to herein as $FP_{18}$. However, the actual content and arrangement of a particular set of imaging optics can vary.

A patterned semiconductor wafer 12 featuring a plurality of wafer dies 14, is placed and aligned on a continuous moving XY translation stage 16 to impart motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging optics 18 in a serpentine (or other) pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution.

In this example, illumination system 26 includes a repetitively pulsed laser 32, a laser beam expander 34, a laser beam light path 36, control/data links 38, and a crystal 40 having non linear optical properties and serving as a 'second harmonic' generating crystal. This type of illumination system enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. Of course, image splitting in accordance with the present subject matter can be used in any inspection system regardless of the particular type, mode, or manner of illumination.

Briefly, FIG. 8 illustrates exemplary components associated with illuminating an object in an inspection system. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 8 shows a bright field illuminating laser source 1300 delivering its output beam 1015 into an optical delivery fiber bundle 1021, preferably by means of a laser to fiber coupler 1150. This optical fiber bundle 1021 provides both uniform illumination on the sample and coherence breaking of the laser illumination. In some embodiments, only a single fiber bundle is used, but it is to be understood that a serially-arranged fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006, and incorporated by reference herein for all purposes.

From the output termination of the fiber bundle 1021, the laser beam is imaged by means of illumination transfer lenses 301, 302 onto the objective lens in use 1201, which is operative to focus the illumination onto a wafer 1100 being inspected. Appropriate alternative objective lenses 1201' can be swung into place on an objective revolver 1200, as is known in the microscope arts. The illumination returned from the wafer is collected by the same objective lens 1201, and is deflected from the illumination path by means of a beam splitter 1202, towards a second beam splitter 1500, from where it is reflected through the imaging lens 1203, which images the light from the wafer onto the detectors of the imager, with one of the detectors represented in FIG. 8 at 1206. In this example, only a single detector and optical path is shown for purposes of example. In practice, the path of light comprising the split portions of the inspection image will, of course, vary. In this example, the second beam splitter 1500 is used to separate the light going to the imaging functionality from the light used in the auto-focus functionality, which is directed by means of the auto-focus imaging lens 1501 to the auto-focus detector 1502.

When conventional dark field illumination is required for the imaging in hand, a dark field side illumination source 1231 is used to project the required illumination beam 1221 onto the wafer 1000. When orthogonal dark field, or obscured reflectance dark field illumination is required for the imaging in hand, an alternative dark field illumination source 1230 is used to project the required illumination beam 1232 via the obscured reflectance mirror 1240 onto the wafer 1000 orthogonally from above. FIG. 8 indicates sources 1300, 1231, and 1230 at different locations. However, any or all of sources 1300, 1230, and 1231 may comprise the same light source, with the bright field, dark field, and obscured reflectance dark field effects achieved through moving the source(s) and/or redirecting illumination to the appropriate angle using one or more optical components. Further, it is to be understood that other arrangements for laser illumination and/or other illumination methods entirely could be used in conjunction with the present subject matter.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. In the example of FIG. 7, an image processing system 99 includes parallel configured image processing channels 90 for image grabbing by an image grabber 92, an image buffer 94, a defect detection unit 96, a defect file 98, and control/data links 101. Image data acquired by focal plane assembly 30 featuring twenty-four two-dimensional CCD matrix photo-detectors 52 is processed in parallel, whereby each of the twenty-four CCD matrix photo-detectors 52 communicates separately, in parallel to the other CCD matrix photo-detectors 52 of focal plane assembly 30, with image grabber 92, via twenty-four separate image processing channels 90. Instead of processing image data using a single serial channel of 48 megapixels at a CCD frame speed acquisition rate of 30 times per second, resulting in a single channel with a very high, 1.5 gigapixels per second processing rate, each of the twenty-four separate image processing channels 90 having about 2 megapixels of image data, acquired at a rate of 30 times per second, is used for processing at a moderate rate of 60 megapixels per second. Image processing system 99 is in communication with central control system 20 via control/data links 102

As another example, the tool may be connected to suitable hardware, or image data may be provided to suitable hardware in any other manner.

Any suitable type(s) of analysis may be used to determine the presence or absence of defects. For example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

The above discussion is for purposes of example only with regard to illumination and imaging techniques. The present subject matter can be utilized in the context of any suitable inspection tool. Next, several different embodiments of splitting techniques and splitting apparatus will be discussed. The splitting apparatus can be used to obtain the continuous surface of detectors illustrated above as focal plane assembly 30.

Figure 1:
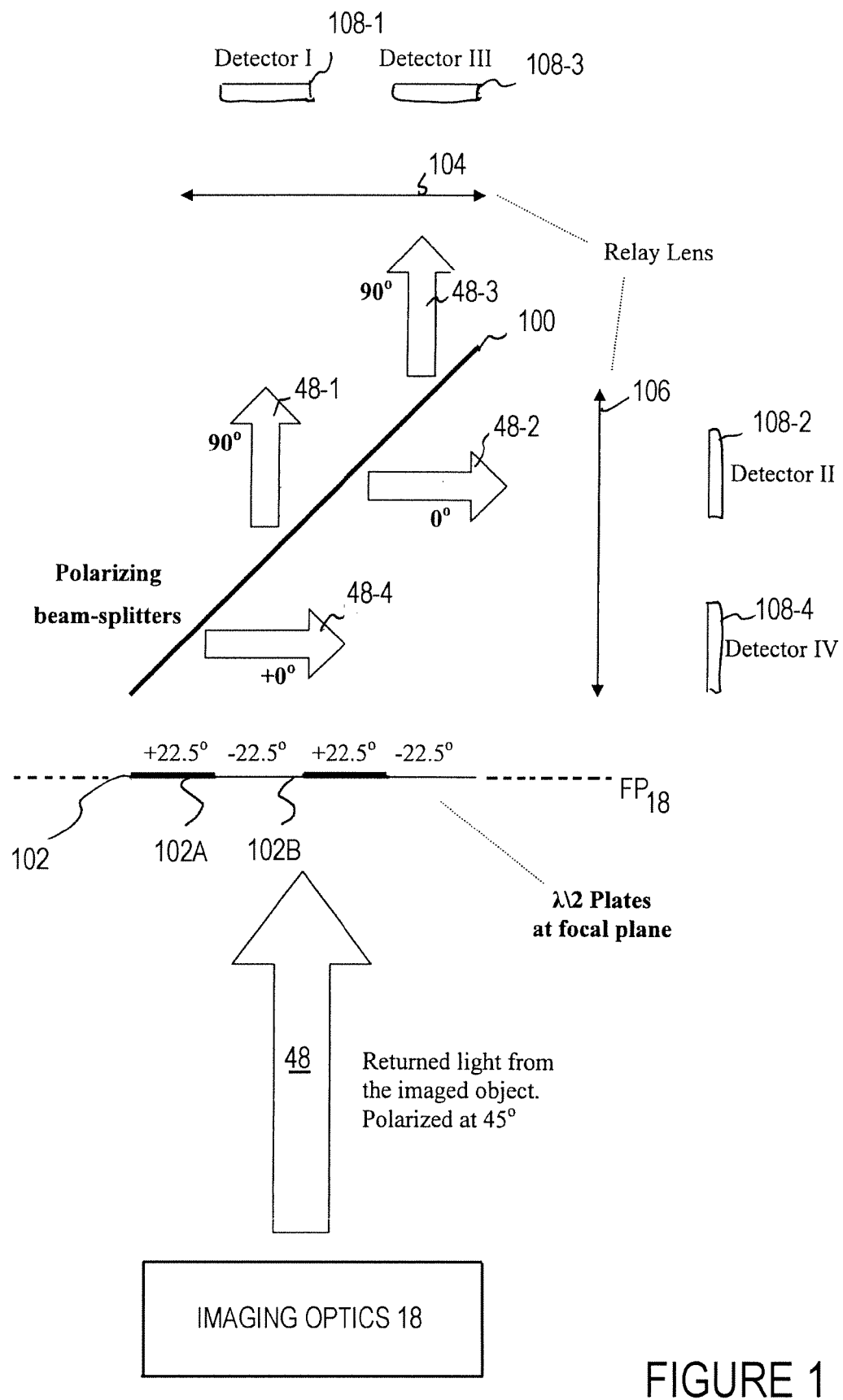
FIG. 1 is a diagram illustrating an exemplary embodiment of a splitting apparatus comprising a beam splitter and an array of components that change the polarization state of light at the focal plane.

FIG. 1 shows an exemplary embodiment of a splitting apparatus comprising a beam splitter 100 and an array 102 of components which change the polarization of incoming light 48. In this example, imaging optics 18 define a focal plane $FP_{18}$ where array 102 is positioned. Furthermore, incoming light 48 comprises light that is polarized, such as at 45 degrees or approximately 45 degrees. For instance, if a laser is used to illuminate the object being inspected, then light comprising the image of the object may already be polarized. However, if light is not polarized, additional components (not shown) can be used to impart a suitable polarization. For instance, polarizers, retarders, filters, or other components could be included in imaging optics 18 and/or elsewhere to polarize incoming light 48 prior to when it arrives at $FP_{18}$. However, if the incoming light is totally non-polarized, the polarizing components will transmit only 50% of the light. Accordingly, use of polarized light in illuminating the object will generally lead to the most advantageous results.

Regardless of the cause(s) of the polarization state of incoming light 48, the polarization state of the light can be used to direct different portions of the light to different detectors. In this example, an array of components 102 is placed at focal plane $FP_{18}$ to rotate the polarization of the light. In this example, the array of components comprises alternating half wave-plates ($\lambda/2$ wave plates) that rotate the polarization +45 degrees and −45 degrees. In FIG. 1, this feature is illustrated by "+22.5°" and "−22.5°", since a wave plate (such as 102a) that rotates the light +45 degrees is within 22.5 degrees and a waveplate (such as 102b) that rotates the light −45 degrees is within −22.5 degrees. In this example, zero (0) degrees is a vector along the x-axis of FIG. 1, and ninety (90) degrees is a vector perpendicular to the plane of FIG. 1 and pointing upward. However, this convention is for purposes of illustration only.

Since the incoming beam 48 is polarized at 45° in this example, after passing through array 102, the various portions of the light corresponding to parts of the image are polarized at different angles. In this example, after the wave-plate array, the light comprises a plurality of portions polarized at 0°, and a plurality of portions polarized at 90°. Polarizing beam splitter 100 is positioned to direct light polarized at 0° differently from light at 90°. In this example, portions of the light polarized at 0° (portions 48-2 and 48-4) are reflected to the right, while portions at 90° (portions 48-1 and 48-3) are transmitted through beam splitter 100. Portions 48-1 and 48-3 are focused to detectors 108-1 and 108-3, respectively, via relay lens 104. Portions 48-2 and 48-4 are focused to respective detectors 108-2 and 108-4 by relay lens 106. Of course, in other embodiments, each detector may have its own relay lens.

Figure 1A:
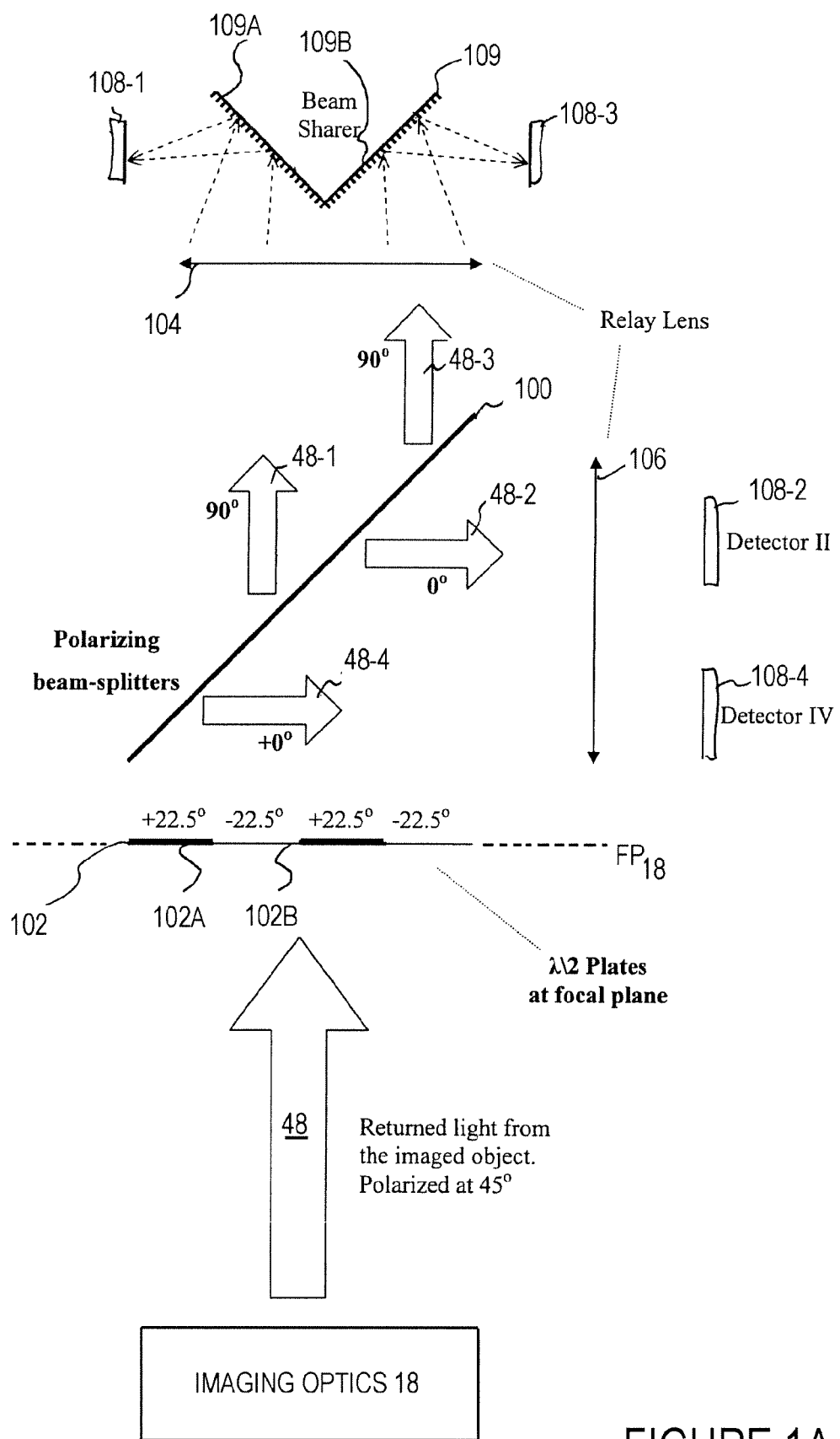
FIG. 1A is a diagram illustrating an exemplary alternate embodiment of the splitting apparatus of FIG. 1.

In this example, the detectors are spaced so that light from the respective portions reaches the respective detectors directly after the relay lenses. However, in other embodiments, different arrangements could be used. For example, a beam sharer 109 comprising a pair of reflective planes 109A and 109B positioned to intersect at the focal plane of a relay lens could be used as shown in FIG. 1A. Other detector arrangements and/or additional beam splitting apparatuses could be used, as well. Use of a beam splitter and/or other suitable splitting device(s) may allow for more flexibility in physically positioning detectors in an inspection tool.

In other embodiments, different rotation angles may be used to obtain the 90° difference between different portions of light. For example, the wave plate array may be configured so that the polarization of incoming light is alternately rotated to +30° and −60°. Furthermore, incoming light 48 may be polarized at angles other than 45°. As one example, the incoming light could be polarized with 0° polarization, and array 102 could be configured to rotate portions of the light to 90° and 0°. Rather than using wave plates for the 0° rotation, transparent windows could be used.

The examples above are for purposes of illustration only. In other embodiments, different polarization, such as circular or elliptical portions and/or other wave-plates such as quarter-wave plates ($\lambda/4$ wave plates) can be used. Furthermore, although incoming light 48 is split into four portions and sent to four detectors, more portions and/or detectors may be used in other embodiments. Additionally, other arrangements of components, such as polarization rotating prisms, could be used to change the polarization of different parts of incoming light 48.

Figure 1B:
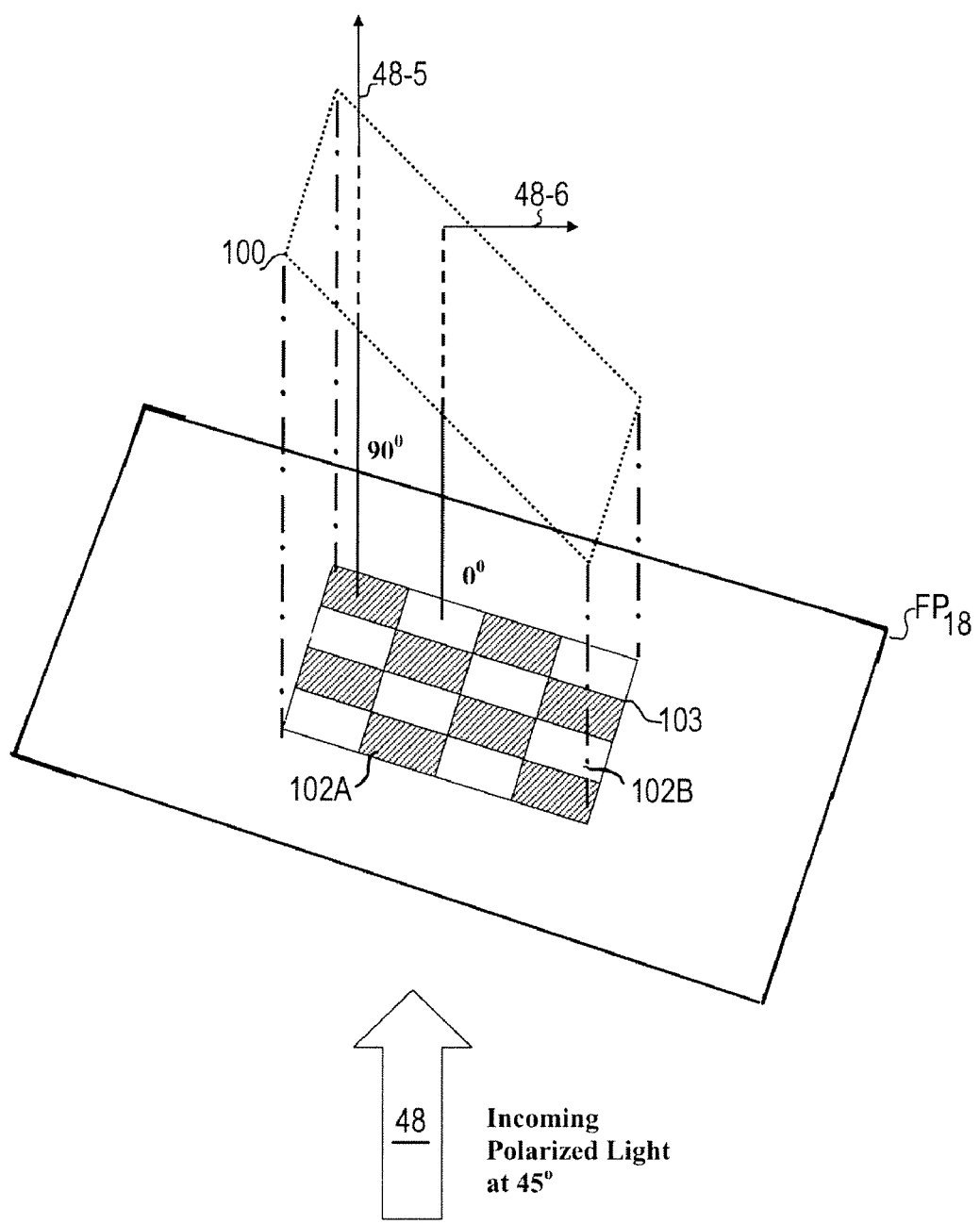
FIG. 1B is a diagram illustrating an exemplary embodiment of a splitting apparatus comprising a beam splitter and a two-dimensional array of components that change the polarization state of light at the focal plane.

Generally, when array 102 is one-dimensional, there is no shadow between the detectors. If array 102 is two-dimensional, though, there can be some shadow effects at the corner of the detectors. This is due to the fact that, when two-dimensional arrays (and two-dimensional detector arrays) are used, the polarization of light which reaches each diagonally adjacent detector is the same, so rays at the detector corners can overlap. In some two-dimensional embodiments, the array features a checkered pattern as shown in FIG. 1B. In this partial perspective view, two-dimensional array 103 comprises a plurality of areas 102a and 102b arranged in a checkered pattern. Different parts of incoming light 48 are polarized by the different areas to 0° and 90°, which are redirected by and transmitted through beam splitter 100, respectively. Two portions, 48-5 (polarized at 90°) and 48-6 (polarized at 0°) are shown in FIG. 1B.

Figure 2:
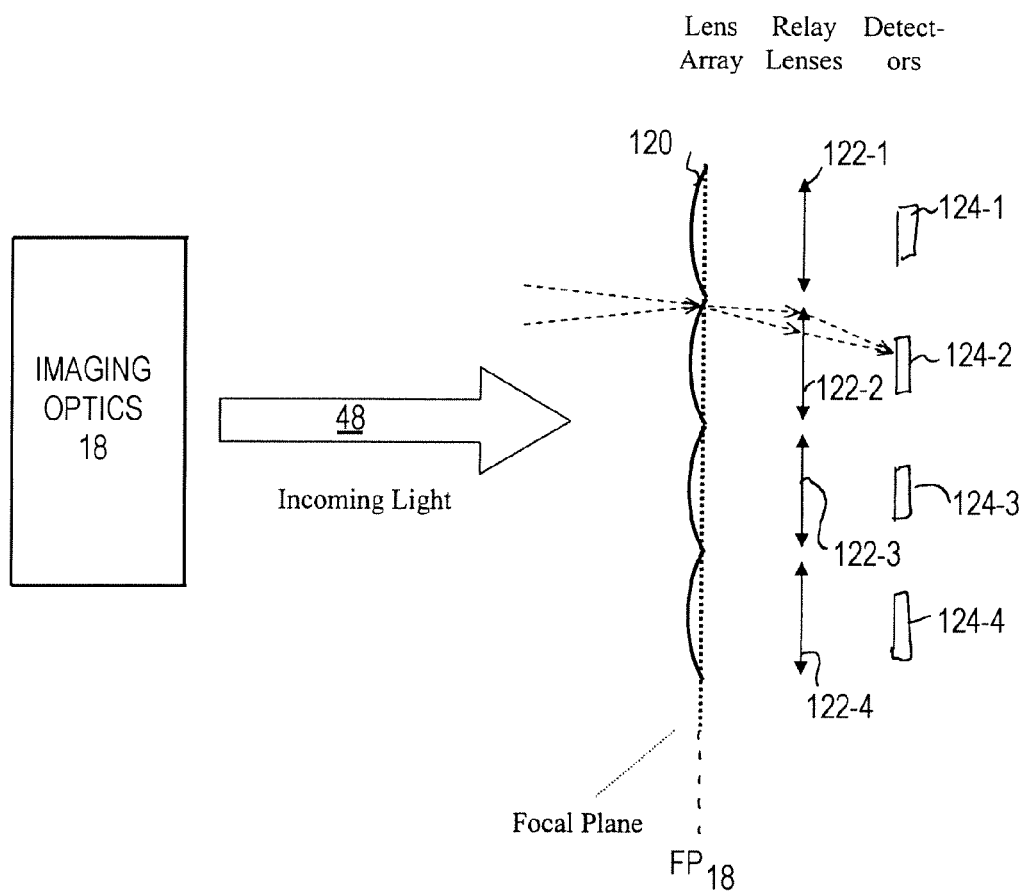
FIG. 2 is a diagram illustrating an exemplary embodiment of a splitting apparatus comprising an array of lenses positioned at the focal plane.

Turning now to FIGS. 2 though 6, other embodiments of splitting apparatuses will be discussed. In these embodiments, various types and arrangements of lenses are used to split light for detection by a matrix of detectors with little or no shadows or illumination loss. As shown in FIG. 2, incoming light from imaging optics 18 encounters a lens array 120 positioned at $FP_{18}$, the focal plane of imaging optics 18. The image in the focal plane is condensed by each lens in the lens array so that rays of each portion are directed to different respective detectors without overlapping. Each lens curves toward imaging optics 18, but the transition between lenses occurs at focal plane $FP_{18}$. The rays of each portion are focused by a relay lens 122-1, 122-2, 122-3, and 122-4 to a respective detector 124-1, 124-2, 124-3, and 124-4. Of course, more or fewer portions and/or detectors could be used. Additionally, relay lenses could be combined in other embodiments.

Figure 3:
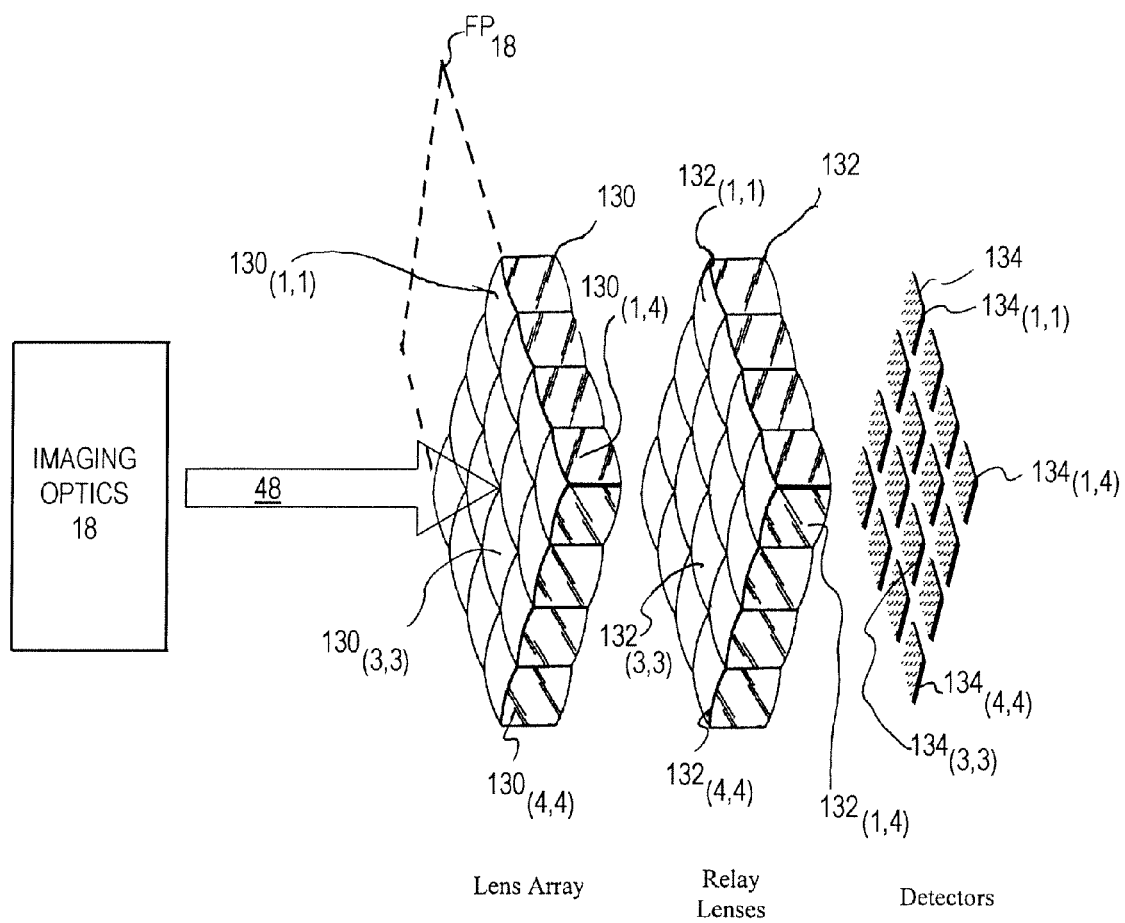
FIG. 3 is a diagram showing a partial perspective view of an exemplary embodiment of a splitting apparatus comprising a two-dimensional array of lenses.

In the one-dimensional case shown in FIG. 2, theoretically the lens array could split incoming light 48 into an unlimited number of images without illumination loss or non-uniformity (assuming ideal components). As shown in FIG. 3, a two-dimensional array of lenses can be used; this, however, results in some illumination loss since the transition between the lenses cannot occur exactly on the focal plane. Thus, areas of non-uniformity occur at the border between detectors.

FIG. 3 is a partial perspective view of an image splitting apparatus comprising a two-dimensional lens array 130, relay lens array 132, and detector matrix 134. As illustrated, incoming light 48 is split into sixteen (16) portions and is directed to a respective detector, each of which detects a respective one of sixteen parts of the image. For instance, light from the part of the image at $FP_{18}$ which enters lens $130_{(1,1)}$ is focused onto detector $134_{(1,1)}$ via relay lens $132_{(1,1)}$. Similarly, light entering lens $130_{(3,3)}$ is focused onto detector $134_{(3,3)}$ via relay lens $132_{(3,3)}$ and light entering lens $130_{(4,4)}$ is focused onto detector $134_{(4,4)}$ via relay lens $132_{(4,4)}$.

The relative location of $FP_{18}$ is also shown in FIG. 3. It should be noted, however, that the depiction of $FP_{18}$ relative to the edges array 130 is not intended to be limiting. Instead, in different embodiments, lens array 130 can extend be the same size, larger than, or smaller than the entire image size at $FP_{18}$.

Figure 4:
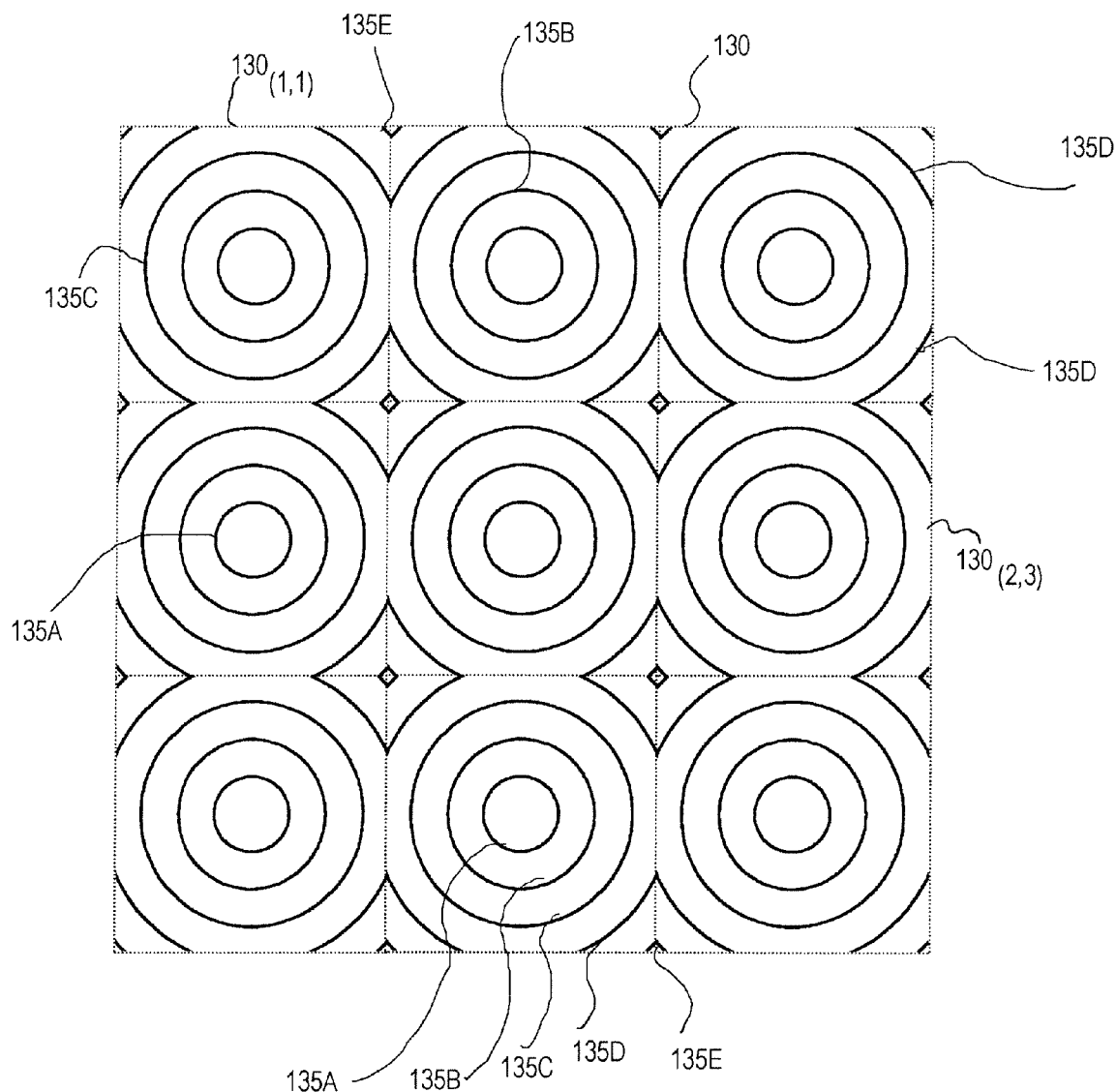
FIG. 4 is an exemplary view of a portion of the array of lenses shown in FIG. 3 as viewed along the axis of light approaching the array.

As was noted above, a two-dimensional lens array allows for splitting an image into parts for detection by a two-dimensional array of detectors at the expense of some non-uniformity due to the fact that transitions between lenses are not all at the focal plane. This can be seen in FIG. 4, which represents a view of a part of lens array 130 as viewed along the path of incoming light 48. The contours representing the curvatures of the lenses are illustrated as 135a (representing the innermost contour), 135b, 135c, 135d, and 135e (representing the outermost contour). The dashed lines represent the borders between lenses and correspond to the division of the light into portions corresponding to the rectangular areas of the image detected by respective detectors. Thus, in this example, a part of array 130 is shown that divides light entering the part into nine portions. Because the array divides the light into rectangular portions and the lenses are circular at the focal plane (due to their spherical or semi-spherical shape), the lens height (i.e. distance from the focal plane) at the border between lenses varies.

Lens array 130, relay lens array 132, and detector matrix 134 can be constructed or assembled in any suitable manner. For instance, either or both lens array 130 and relay lens array 132 may comprise a plurality of discrete lenses bonded or joined together or mechanically held in the desired arrangement at the appropriate location(s). Alternatively, either or both arrays may be formed as a single unit having the desired optical properties.

Figure 5:
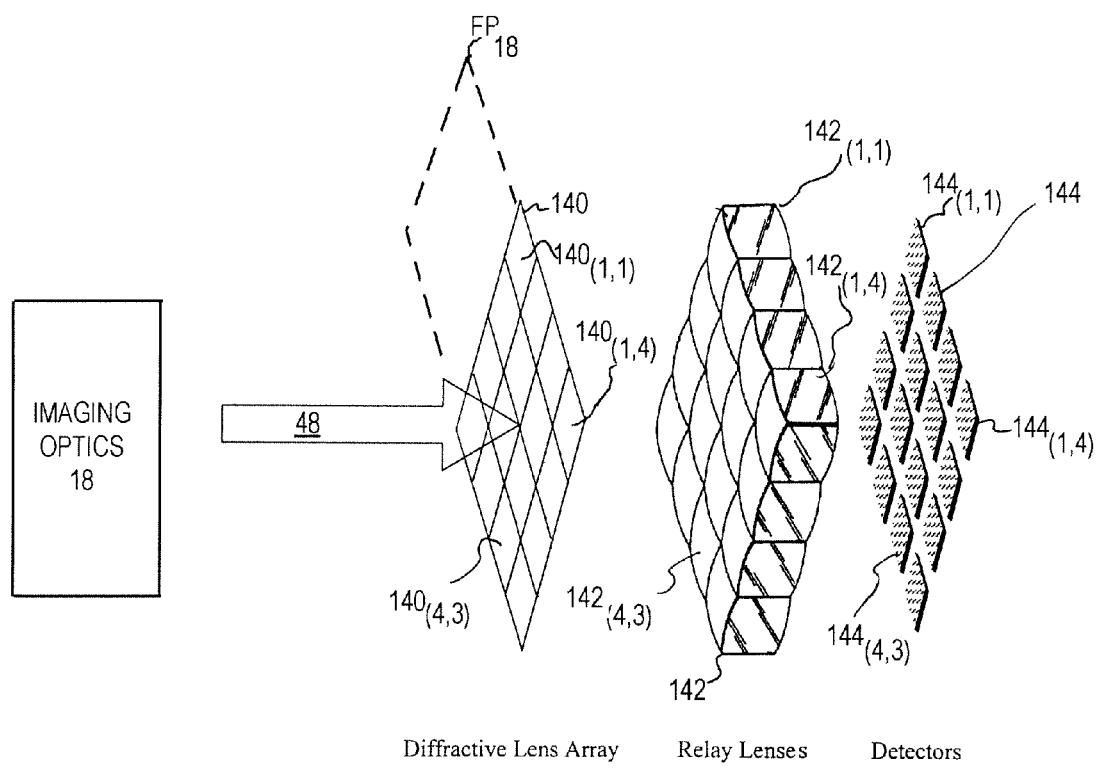
FIG. 5 is a diagram showing a partial perspective view of an exemplary embodiment of a splitting apparatus comprising a two-dimensional array of diffractive lenses.

In some embodiments, non-uniformities at the border between lenses can be reduced or avoided. For instance, diffractive lenses with a homogenous width can be used so that the borders are in focus along the entire length of the array. FIG. 5 illustrates an array 140 of diffractive lenses positioned at $FP_{18}$, with respective diffractive lenses dividing the light into portions that are focused by lenses of relay lens array 142 onto respective two-dimensional detectors in detector matrix 144. For instance, light from the part of the image at $FP_{18}$ which enters lens $140_{(1,1)}$ is focused onto detector $144_{(1,1)}$ via relay lens $142_{(1,1)}$. Similarly, light entering lens $140_{(4,3)}$ is focused onto detector $144_{(4,3)}$ via relay lens $142_{(4,3)}$. Since the diffractive lenses are (substantially) flat, non-uniformities due to height differences are largely avoided. For instance, the active thickness of each lens (i.e. the width of the material that condenses the light) is about on the same order of magnitude as the wavelength of the light. Thus, the rays of light comprising the different portions are condensed before overlapping, and the borders of the parts of the image are in focus along the entire length of each part.

As another example of using flat lenses, graded-index (GRIN) lenses can be used in the lens array.

The relative location of $FP_{18}$ is also shown in FIG. 5. It should be noted, however, that the depiction of the boundaries of $FP_{18}$ relative to the edges array 140 is not intended to be limiting. Instead, in different embodiments, lens array 140 can extend along the entirety of $FP_{18}$ or along only one or more parts of $FP_{18}$.

Figure 6:
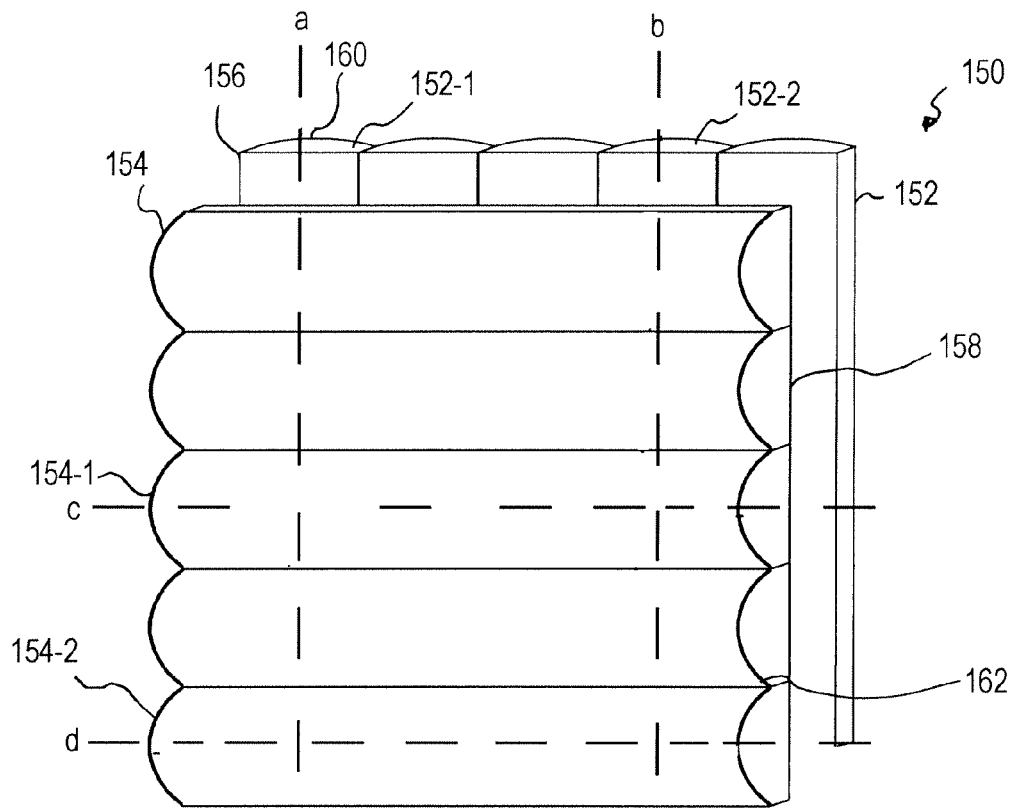
FIG. 6 is a diagram showing an exemplary embodiment of a splitting apparatus comprising a plurality of arrays of lenses, each array comprising a plurality of partially-cylindrical lenses.

As an alternative to using flat lenses, a structure comprising cylindrical or partially-cylindrical lenses can be used as shown in FIG. 6. FIG. 6 illustrates a partial perspective view of a splitting apparatus 150 comprising a pair of lens arrays 152 and 154 arranged in sequence. Each array 152 and 154 comprises a plurality of partially-cylindrical lenses placed alongside one another. Exemplary lenses 152-1 and 152-2 of array 152 are illustrated, along with lenses 154-1, and 154-2 of array 154. Of course, each array may comprise more or fewer lenses.

In this example, each lens has a flat side and a convex side. For instance, cylindrical lens 152-1 has a flat side 156 and a convex side 160. Convex side 160 curves about an axis A which lies in the plane of flat side 156. Axis B of lens 152-2 is shown, along with axes C and D of lenses 154-1 and 154-2, respectively. The flat side of each lens in array is in the same plane as the other flat sides, and the axes of the various lenses in an array are parallel to one another. Furthermore, in this configuration, the axes of the lenses in array 152 are perpendicular to the axes of the lenses in the array 154, and arrays 152 and 154 are positioned with their flat sides facing one another and at the focal plane $FP_{18}$ of imaging optics 18. Accordingly, the lens height (i.e. distance from the focal plane) at the boundary between split portions is the same across both sides of the boundary. Thus, the border areas between parts of the image remains in focus.

The curved and flat sides may correspond to the physical shape of the lens in some embodiments. In some embodiments, through, the actual lenses may diffractive or graded index lenses that are physically flat on both sides, but are configured so that, optically, the lens behaves as if the other side features a curved surface.

Figure 6A:
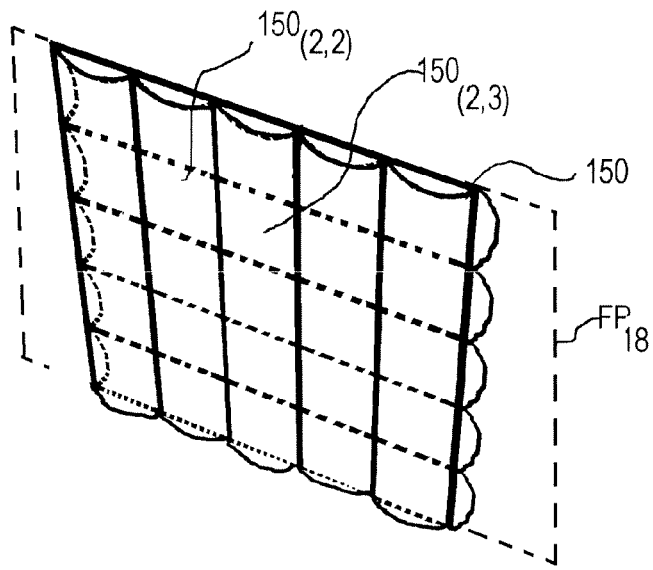
FIG. 6A is a partial perspective view of the splitting apparatus shown in FIG. 6.

FIG. 6A shows another view of splitting apparatus 150. In this view, the lens arrays are configured to divide incoming light into twenty-five (25) portions. Each portion is defined by the intersection of a lens from one of the arrays. The borders of each portion correspond to the intersections between the convex side of each lens with its flat side. In this example, two exemplary portions $150_{(2,2)}$ and $150_{(2,3)}$ are shown of the twenty-five total portions created in this embodiment. The cylindrical lenses may be of any suitable type or material, including diffractive or graded index lenses.

The relative location of $FP_{18}$ is also shown in FIG. 6A. It should be noted, however, that the depiction of $FP_{18}$ relative to the edges array 150 is not intended to be limiting. Instead, in different embodiments, lens array 150 can extend to be the same size, larger than, or smaller than the entire image size at $FP_{18}$.

In any of the embodiments of the present subject matter, the individual relay lenses may be replaced by any suitable optics that contain lenses mirrors, and/or other components. The optics may have any kind of magnification, such as 1:1, enlarging or shrinking. Further, in any of the embodiments, the splitting apparatus can extend can extend to be the same size, larger than, or smaller than the entire image size at $FP_{18}$.

In several examples, images were split into a number of portions, with each portion corresponding to a different detector. However, it will be understood that, for a given splitting apparatus, the number of portions may or may not ultimately correspond to the number of detectors. For instance, if a splitting apparatus is cascaded with other splitting apparatuses, then the number of detectors will exceed the number of portions created by the first splitting apparatus. Moreover, it will be understood that any embodiment of a splitting apparatus discussed herein can be cascaded any suitable number of times with any other splitting apparatus.

Exemplary detectors were also discussed in several examples above. It will be understood that any suitable type, or combination of types, of detectors can be used, and the particular architecture or principles of operation for detectors can vary. For example, suitable two-dimensional detectors include, but are not limited to, CCD or CMOS detectors.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. An inspection system configured to create an image of an object at a focal plane, the semiconductor inspection system comprising:
    a set of imaging optics configured to create an image of an object at a focal plane;
    at least two two-dimensional detectors; and
    at least one splitting apparatus positioned at the focal plane and configured to split the image of the object at the focal plane into a plurality of portions and direct at least one portion to a two-dimensional detector, wherein the splitting apparatus comprises two sequential arrays, each array comprising a plurality of at least partially cylindrical lenses positioned alongside one another.

2. The inspection system set forth in claim 1, wherein:
    the at least one splitting apparatus comprises an array of components configured to change portions of the light comprising different parts of the image so that at least one portion has a different polarization from another portion; and
    the splitting apparatus comprises at least one beam splitter that directs at least one portion of light to a detector based on the polarization state of the light.

3. The inspection system set forth in claim 2, wherein:
    the array comprises components that rotate the polarization state of light entering the components; and
    each component is adjacent to a component of another type such that the difference between rotation angles imparted by a pair of adjacent components is ninety degrees.

4. The inspection system set forth in claim 2, wherein the array is two-dimensional.

5. The inspection system set forth in claim 1, wherein the splitting apparatus comprises an array of lenses.

6. The inspection system set forth in claim 5, wherein the array of lenses comprises a plurality of graded index lenses.

7. The inspection system set forth in claim 5, wherein the array of lenses comprises a two-dimensional lens array.

8. The inspection system set forth in claim 5, wherein the lenses of the array comprise diffractive lenses.

9. The inspection system set forth in claim 8, wherein the array of lenses comprises a two-dimensional diffractive lens array.

10. The inspection system set forth in claim 1, wherein:
    the cylindrical lenses each comprise a flat side and a convex side curving outward about a respective axis laying in a plane containing the flat side, the axis of each cylindrical lens in the same array being parallel to one another; and
    the flat side of each array faces the flat side of the other array.

11. The inspection system set forth in claim 1, wherein at least one of the cylindrical lenses comprises a diffractive lens or a graded index lens.

12. The inspection system set forth in claim 1, wherein each array is positioned so that the axes of the convex side of the lenses in one array are perpendicular to the axes of the convex side of the lenses in the other array.

13. The inspection system set forth in claim 2, further comprising: at least one illumination source; and
 a transporter configured to impart relative motion between the object and the focal plane so that the portion of the object that is in view of the focal plane can be varied.

14. The inspection system set forth in claim 13, wherein the at least one illumination source comprises a laser configured to illuminate the object with polarized light.

15. The inspection system set forth in claim 13, further comprising at least one polarizing element configured to polarize light comprising the image of the object before the light reaches the array of components.

16. A method of inspecting an object, the method comprising:
 obtaining an image of at least a portion of an object, wherein obtaining comprises collecting light rays scattered, reflected, or diffracted by the object by way of a set of imaging optics, the set of imaging optics defining a focal plane;
 splitting the image into a plurality of portions using a splitting apparatus comprising two sequential arrays, each array comprising a plurality of at least partially cylindrical lenses positioned alongside one another;
 changing the polarization of portions of the light comprising the image, using the splitting apparatus, so that a portion corresponding to at least one part of the image has a different polarization than a portion corresponding to another part of the image;
 directing at least one portion of light to a two-dimensional detector based on the polarization of the light; and
 obtaining data representing each portion of the image as represented by light incident at each two-dimensional detector.

17. The method set forth in claim 16, wherein changing the polarization of portions of the light comprises passing the light through an array of components of configured to rotate the polarization of alternate portions of the light in opposite directions.

18. The method set forth in claim 17, wherein the array of components comprises a half-wave plate.

19. The method set forth in claim 17, wherein the array of components is two-dimensional.

20. A method of inspecting an object, the method comprising:
 obtaining an image of at least a portion of an object, wherein obtaining comprises collecting light rays scattered, reflected, or diffracted by the object by way of a set of imaging optics, the set of imaging optics defining a focal plane;
 splitting light comprising the image into a plurality of portions, each portion corresponding to a respective part of the image by passing the light through at least one lens array comprising a plurality of cylindrical lenses each comprising a flat side and a convex side, the convex side of each lens comprising a portion curving about a respective axis laying in a plane containing the flat side, with the axes of each cylindrical lens in the same array being parallel to one another;
 directing each portion to a respective detector in an array comprising a plurality of two-dimensional detectors by passing the light through at least one lens array; and
 obtaining data representing each part of the image as represented by light incident at each two-dimensional detector.

21. The method set forth in claim 20, wherein the lens array comprises a plurality of diffractive lenses.

22. The method set forth in claim 20, wherein the at least one lens array comprises a pair of arrays of cylindrical lenses, the pair of arrays configured so that the flat side of each array faces the flat side of the other array and the axes of the lenses of each array are perpendicular to the axes of the lenses of the other array.

\* \* \* \* \*